US006703540B1

(12) United States Patent
Jacks et al.

(10) Patent No.: US 6,703,540 B1
(45) Date of Patent: Mar. 9, 2004

(54) TRANSFORMATION OF PLANTS WITH A CHLOROPEROXIDASE GENE TO ENHANCE DISEASE RESISTANCE

(75) Inventors: Thomas J. Jacks, Metairie, LA (US); Jeffrey W. Cary, Covington, LA (US); Kanniah Rajasekaran, Metairie, LA (US); Thomas E. Cleveland, III, Mandeville, LA (US); Karl-Heinz Van Pee, Bannewitz (DE)

(73) Assignee: The United States of America as represented by the Secretary of Agriculture, Washington, DC (US)

(*) Notice: Subject to any disclaimer, the term of this patent is extended or adjusted under 35 U.S.C. 154(b) by 0 days.

(21) Appl. No.: 09/522,401

(22) Filed: Mar. 9, 2000

(51) Int. Cl.[7] ........................ C12N 15/09; C12N 15/31; C12N 15/82; A01H 5/00; A01H 5/10

(52) U.S. Cl. ........................ 800/278; 800/288; 800/298; 800/295; 800/314; 435/419; 435/468; 435/320.1; 536/23.2; 536/24.1; 536/23.7

(58) Field of Search ................................ 800/279, 278, 800/298, 314, 288, 295; 536/23.2, 24.1, 23.7; 435/419, 468, 320.1

(56) References Cited

U.S. PATENT DOCUMENTS 4,956,282 A * 9/1990 Goodman et al. ....... 435/69.51
5,773,696 A * 6/1998 Liang et al. ................ 800/205

OTHER PUBLICATIONS

Cleveland, T.E., et al., "Identification of Traits for Enhancing Crop Resistance to Preharvest Aflatoxin Contamination", USDA CRIS Report Project No. 6435–42000–009–00D for Fiscal Year 1995, Published Mar., 1995.

Cleveland, T.E., et al., "Aflatoxin Control Through Addition Enhancement of Antifungal Genes in Corn and Cotton", USDA CRIS Report Project No. 6435–42000–012–00D for Fiscal Year 1997, Published Mar., 1997.

Jacks, T.J., et al., "Potential of Animal Myeloperoxidase to Protect Plants from Pathogens", *Biochemical and Biophysical Research Communications*, vol. 178(3), pp. 1202–1204, Aug. 15, 1991.

Jacks, T.J., et al., "Superoxide, Hydrogen Peroxide, and the Respiratory Burst of Fungally Infected Plant Cells", *Molecular and Cellular Biochemistry*, vol. 158, pp. 77–79, 1996.

Jacks, T.J., et al., "Effects of Chloroperoxidase and Hydrogen Peroxide on the Viabilities of *Aspergillus flavus* Conidiospores", *Molecular and Cellular Biochemistry*, vol. 195, pp. 169–172, 1999.

Pfeifer, O., et al., "Molecular Cloning and Sequencing of a Non–haem Bromoperoxidase Gene from *Streptomyces aureofaciens* ATCC 10762", *J. General Microbiology*, vol. 138, pp. 1123–1131, 1992.

Picard, M., et al., "Metal–Free Bacterial Haloperoxidases as Unusual Hydrolases: $H_2O_2$ by the Formation of Peracetic Acid", *Angew. Chem. Int. Ed. Engl.*, vol. 36(11), pp. 1196–1199, 1997.

Mehdy, M.C., et al., "The Role of Activated Oxygen Species in Plant Disease Resistance", *Physiologia Plantarum*, vol. 98, pp. 365–374, 1996.

Wiesner, W., et al., "Purification and Properties of Bromoperoxidase from *Pseudomonas pyrrocinia", J. Biol. Chem.*, vol. 366, pp. 1085–1091, Dec. 1985.

Wiesner, W., et al., "Purification and Characterization of a Novel Bacterial Non–heme Chloroperoxidase from *Pseudomonas pyrrocinia", J. Biological Chemistry*, vol. 263(27), pp. 13725–13732, Sep. 25, 1988.

Wojtaszek, Przemyslaw, "Oxidative Burst: An Early Plant Response to Pathogen Infection", *J. Biochem.*, vol. 322, pp. 681–692, 1997.

Wolfframm, C., et al., "Chloroperoxidase–encoding Gene from *Pseudomonas pyrrocinia*: Sequence, Expression in Heterologous Hosts, and Purification of the Enzyme", *Gene*, vol. 130, pp. 131–135, 1993.

Wolfframm, C., et al., "Cloning and High–level Expression of a Chloroperoxidase Gene from *Pseudomonas pyrrocinia* in *Escherichia coli", FEBS Letters*, vol. 238(2), pp. 325–328, Oct. 1988.

Van Pee, K–H., "Biosynthesis of Halogenated Metabolites by Bacteria", *Annu. Rev. Microbiol.*, vol. 50, pp. 375–399, 1996.

* cited by examiner

*Primary Examiner*—Phuong T. Bui
*Assistant Examiner*—Medina A. Ibrahim
(74) *Attorney, Agent, or Firm*—John D. Fado; Evelyn M. Rabin

(57) ABSTRACT

The present invention provides a method of making plants resistant to plant pathogens by transformation of host cells with a nucleic acid encoding a nonheme haloperoxidase. Transgenic plants which express a nonheme chloroperoxidase thereby resulting in enhanced resistance to phytopathogens are provided.

35 Claims, 10 Drawing Sheets

PCR genomic DNA from halo transgenic cotton plants

RT-PCR of total RNA of halo transgenic cotton plants

SEQUENCE LISTING

```
<160> NUMBER OF SEQ ID NOS: 6

<210> SEQ ID NO 1
<211> LENGTH: 837
<212> TYPE: DNA
<213> ORGANISM: Pseudomonas pyrrocinia

<400> SEQUENCE: 1

atgccatacg tcactacgaa ggataacgtc gagatcttct acaaggactg gggcccgaag    60

gacgcacagc ccatcgtctt ccatcatggc tggccgttgt cgggcgacga ctgggatgcg   120

cagatgctct tcttcgttca gaagggctat cgcgtgattg cgcacgaccg gcgcggccac   180

ggccggtcgg cgcaggtgtc ggacggccat gacatggatc attacgcagc ggacgcgttc   240

gcggtcgtcg aagcgctcga cctgcgcaat gcggtgcata tcggtcattc gaccggcggc   300

ggcgaagtgg cccgctacgt cgcgaagcac ggccagccgg ccggtcgtgt cgcgaaggcg   360

gtgctggtca gcgcggtgcc gccgctgatg ctgaaaaccg aatcgaaccc cgaaggcttg   420

ccgatcgagg tgttcgacgg cttccggaag gcgctcgccg acaatcgcgc acagttcttc   480

ctcgacgtgc cgaccggccc gttctacggt ttcaaccggg ccggcgcgac ggtgcatcag   540

ggcgtcatcc ggaactggtg gcggcagggg atggagggca gcgcgaaggc gcactacgac   600

ggcatcaagg cgttttcgga aacggatcag accgaggacc tgaagtcgat caccgtcccg   660

acgctcgtgc tgcatggcga agacgaccag atcgtgccga tcgcggatgc cgcgctgaag   720
```

-continued tcgatcaagc tgctgcagaa cggcacgctc aagacgtatc cgggttattc gcacggcatg 780
ctgacggtga acgcggacgt tctcaacgcc gacctgctgg cgttcgtgca ggcgtaa 837

<210> SEQ ID NO 2
<211> LENGTH: 278
<212> TYPE: PRT
<213> ORGANISM: Pseudomonas pyrrocinia

<400> SEQUENCE: 2

```
Met Pro Tyr Val Thr Thr Lys Asp Asn Val Glu Ile Phe Tyr Lys Asp
  1               5                  10                  15

Trp Gly Pro Lys Asp Ala Gln Pro Ile Val Phe His His Gly Trp Pro
             20                  25                  30

Leu Ser Gly Asp Asp Trp Asp Ala Gln Met Leu Phe Phe Val Gln Lys
         35                  40                  45

Gly Tyr Arg Val Ile Ala His Asp Arg Arg Gly His Gly Arg Ser Ala
     50                  55                  60

Gln Val Ser Asp Gly His Asp Met Asp His Tyr Ala Ala Asp Ala Phe
 65                  70                  75                  80

Ala Val Val Glu Ala Leu Asp Leu Arg Asn Ala Val His Ile Gly His
                 85                  90                  95

Ser Thr Gly Gly Gly Glu Val Ala Arg Tyr Val Ala Lys His Gly Gln
            100                 105                 110

Pro Ala Gly Arg Val Ala Lys Ala Val Leu Val Ser Ala Val Pro Pro
        115                 120                 125

Leu Met Leu Lys Thr Glu Ser Asn Pro Glu Gly Leu Pro Ile Glu Val
    130                 135                 140

Phe Asp Gly Phe Arg Lys Ala Leu Ala Asp Asn Arg Ala Gln Phe Phe
145                 150                 155                 160

Leu Asp Val Pro Thr Gly Pro Phe Tyr Gly Phe Asn Arg Ala Gly Ala
                165                 170                 175

Thr Val His Gln Gly Val Ile Arg Asn Trp Trp Arg Gln Gly Met Glu
            180                 185                 190

Gly Ser Ala Lys Ala His Tyr Asp Gly Ile Lys Ala Phe Ser Glu Thr
        195                 200                 205

Asp Gln Thr Glu Asp Leu Lys Ser Ile Thr Val Pro Thr Leu Val Leu
    210                 215                 220

His Gly Glu Asp Asp Gln Ile Val Pro Ile Ala Asp Ala Ala Leu Lys
225                 230                 235                 240

Ser Ile Lys Leu Leu Gln Asn Gly Thr Leu Lys Thr Tyr Pro Gly Tyr
                245                 250                 255

Ser His Gly Met Leu Thr Val Asn Ala Asp Val Leu Asn Ala Asp Leu
            260                 265                 270

Leu Ala Phe Val Gln Ala
        275
```

<210> SEQ ID NO 3
<211> LENGTH: 23
<212> TYPE: DNA
<213> ORGANISM: Pseudomonas pyrrocinia

<400> SEQUENCE: 3
aagctttgcc atacgtcact acg 23

<210> SEQ ID NO 4

-continued

```
<211> LENGTH: 22
<212> TYPE: DNA
<213> ORGANISM: Pseudomonas pyrrocinia

<400> SEQUENCE: 4

gagctctacg cctgcacgaa cg                                          22


<210> SEQ ID NO 5
<211> LENGTH: 22
<212> TYPE: DNA
<213> ORGANISM: Pseudomonas pyrrocinia

<400> SEQUENCE: 5

tcattgcgat aaaggaaagg cc                                          22


<210> SEQ ID NO 6
<211> LENGTH: 21
<212> TYPE: DNA
<213> ORGANISM: Pseudomonas pyrrocinia

<400> SEQUENCE: 6

gattcggttt tcagcatcag c                                           21
```

TRANSFORMATION OF PLANTS WITH A CHLOROPEROXIDASE GENE TO ENHANCE DISEASE RESISTANCE

BACKGROUND OF THE INVENTION

1. Field of the Invention

The present invention relates generally to the protection of plants against phyto-pathogens. In one aspect it provides transgenic plants which have enhanced resistance to phyto-pathogens. It further provides methods for protecting plants against phytopathogens.

2. Description of the Relevant Art

Living organisms possess several inherent defense mechanisms to fight microbial pathogens. One of the chronologically earliest responses to invasion is a respiratory burst that produces two reactive oxygen species that are microbicidal: superoxide and hydrogen peroxide (Mehdy, M. C. 1994. *Plant Physiol.* 105: 467–472; Wojtaszek, P. 1997. *Biochem. J.* 322: 681–692). Hydrogen peroxide and its products from reactions with endogenous metabolites possess relatively moderate antimicrobial activity (Doke et al. 1991. Active Oxygen/Oxygen Stress and Plant Metabolism, E. Pell et al. (Eds.). Am. Soc. Plant Physiol., Rockville Md.). Deadlier antimicrobial compounds such as hypohalites are generated from hydrogen peroxide in some bacterial organisms that contain haloperoxidases, for example, chloroperoxidases. Animals contain myeloperoxidase; and in the presence of myeloperoxidase, animal cells, too, can convert hydrogen peroxide to a much stronger antimicrobial compound, hypochlorous acid (HOCl), i.e., $$H_2O_2+HCl \rightarrow H_2O+HOCl \qquad (1)$$

Plants routinely become infected by fungi, viruses, and bacteria; however, vascular plants lack haloperoxidases such as myeloperoxidase and consequently lack this potent system of antimicrobial and antifungal protection. Although plants lack this endogenous haloperoxidase-based method of defense, plant fungi are sensitive to the effects of these haloperoxidases in experiments in vitro. Jacks et al. (1991. *Biochem. Biophys. Res. Commun.* 178: 1202–1204) have shown that the conversion of hydrogen peroxide to hypochlorite, catalyzed by myeloperoxidase, results in as much as a 90-fold increase in lethality against the plant fungus *Aspergillus flavus* in vitro, suggesting the possibility that plants transformed with a haloperoxidase gene could possess the advantage of an increased disease resistance to phytopathogens. However, for a transformation strategy involving the enzymes, myeloperoxidase or most haloperoxidases, to be successful, the addition of a plethora of genes coding for the multi-component synthesis of each species specific heme-containing prosthetic group is a necessary requirement (Pfeifer et al. 1992. *J. Gen. Microbiol.* 138: 1123–1131; van Pee, K-H. 1996. *Annu. Rev. Microbiol.* 50: 375–399) because these heme derivatives are not available in plants.

Accordingly, this invention provides an alternative strategy, specifically, transformation with a gene encoding a functional yet heme-free haloperoxidase. Such a strategy therefore bypasses the need for including nucleic acid sequences which encode additional components related to specific heme groups.

Presently, plant breeding and biocontrol programs, as well as the development of new antimicrobial agents and fungicides, are disease preventive methods that are being successfully practiced to protect crops. However, it is well known that rapid genetic changes take place in pathogenic organisms. Such evolutionary changes result in the resistance genes of the host quickly becoming ineffective. These facts, together with cost, time considerations, and actual field results, necessitate the constant search for novel methods and reagents for protecting agricultural crops.

SUMMARY OF THE INVENTION

We have discovered that the expression of a gene encoding a nonheme haloperoxidase in a plant provides protection to the plant against phytopathogens.

In accordance with this discovery, it is an object of the invention to provide a plant transformed with a gene which encodes a nonheme haloperoxidase and which is expressed to confer protection to the plant against phytopathogens. In particular, a plant in which a nonheme chloroperoxidase is expressed is provided.

Another object of the invention is to provide a method of transforming a plant with a gene capable of expressing a nonheme haloperoxidase sufficient to confer protection to the plant against phytopathogens. A method of transforming a plant with a gene encoding a nonheme chloroperoxidase is particularly provided.

Plant transformation vectors comprising the gene which encodes the nonheme haloperoxidase of the invention are also provided, as are plant cells transformed by these vectors, and plants and their progeny containing the genes.

It is an additional object of the invention to provide a host cell containing the DNA of the invention, wherein said host cell is a bacterial cell, in particular, an *Agrobacterium tumefaciens* cell.

Still further, it is an object of the invention to engineer the DNA molecules of the invention to allow in the plant for constitutive expression, expression in response to an inducer, expression in particular tissues, and expression at particular stages of development.

Other objects and advantages of this invention will become readily apparent from the ensuing description.

DETAILED DESCRIPTION OF THE INVENTION

Figure 1:
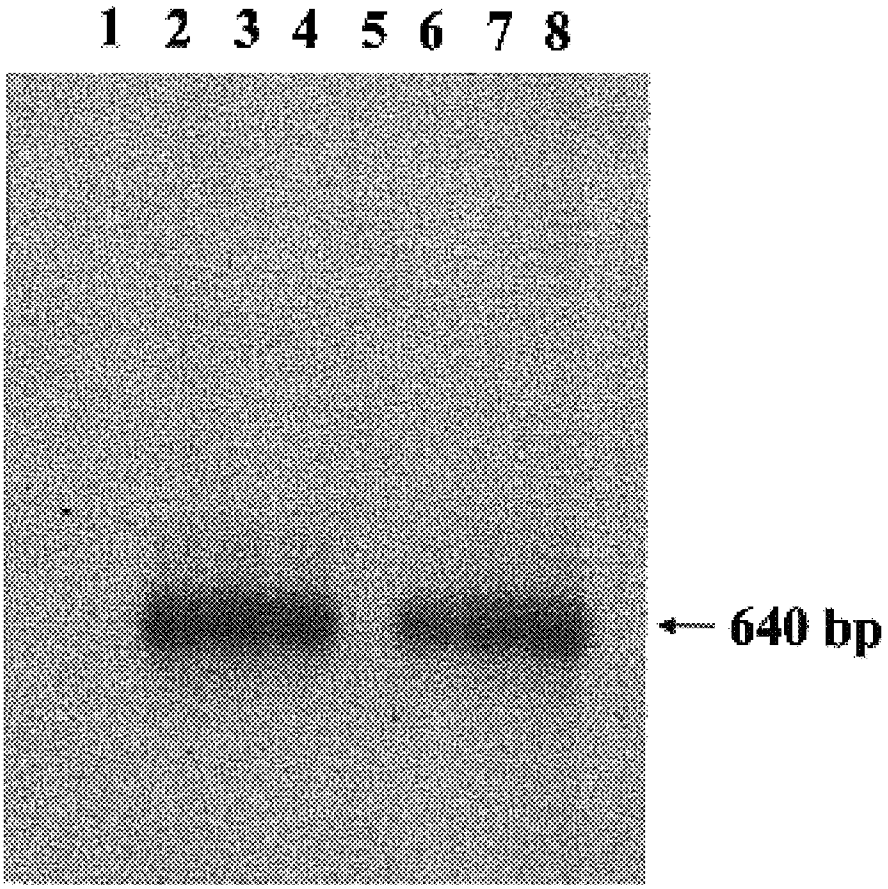
FIG. 1 shows a southern hybridization of DNA products from the PCR amplification of genomic DNA of tobacco tissue transformed with KYLX-cpo. Primers were designed to amplify approximately a 640 bp region spanning from within the CaMV 35S promoter to 400 bp internal to the cpo gene. $^{32}P$-labeled 836 bp cpo gene PCR product was used as a probe. Lanes:1, no DNA negative control; 2, H1; 3, H2; 4, H3; 5, tobacco negative control; 6, H5; 7, H6; 8, H7.

This invention provides a transgenic plant displaying resistance to phytopathogens as a result of the expression of a bacterial heme free haloperoxidase gene. In particular, the invention provides a method of making a recombinant pathogen-resistant plant comprising transforming plants with a nucleic acid encoding a metal-free nonheme haloperoxidase gene. Particular bacterial haloperoxidases have been discovered which do not require heme prosthetic groups or even metal ion cofactors (Picard et al. 1997. *Angew. Chem. Int. Ed. Engl.* 36: 1196–1199). The nonheme haloperoxidase gene of the invention is preferably a metal-free nonheme chloroperoxidase gene, most preferably the metal-free non heme CPO-P gene of *Pseudomonas pyrrocinia* (Wolfframm et al., 1993. *Gene* 130: 131–135). Particularly provided are transgenic plants which express the chloroperoxidase CPO-P.

An advantage of plants thus transformed is that these particular haloperoxidases have the advantage of catalyzing not only the formation of hypohalites from hydrogen peroxide (according to reaction (1), above), but also the formation of peracetic acid. Hypohalite formation can therefore additionally result from the oxidation of alkyl acids with hydrogen peroxide to form peracids followed by the spontaneous oxidation of halides by peracids (van Pee, K-H., supra):

$$AcOH + H_2O_2 \rightarrow H_2O + AcOOH \quad (2)$$

$$AcOOH + X^- \rightarrow AcOH + {}^-OX \quad (3)$$

where $^-$OX is a hypohalite, AcOH is acetic acid, and ACOOH is peracetic acid. Both hypohalites and peracetic acid are strong antimicrobial agents. Such haloperoxidases belong to a class of enzymes that has been classified by the Enzyme Commission (E.C.) into that group of oxidoreductases referred to as E.C.1.11.1.10. According to the halide ions they can oxidize, haloperoxidases are designated as chloroperoxidases, bromoperoxidases, and iodoperoxidases.

Presence of these potent enzymic reaction products of the chloroperoxidase, i.e., hypohalite and peracetic acid, results in up to 120 fold greater lethality than that resulting from hydrogen peroxide (Table 1). Further, transgenic plants transformed with the particular chloroperoxidase, CPO-P, which generates at least these two potent enzymic reaction products, have the advantage of an increased resistance to plant pathogens, microbial and fungal.

TABLE 1

Comparative Lethalities of Oxidants to *Aspergillus flavus*.

| Oxidant | $LD_{50}$ (mM)$^a$ |
|---|---|
| $H_2O_2$ | 18.00 |
| HOCl | 0.30 |
| HOOAc | 0.15 |
| $H_2O_2$ plus CPO | 0.60 |
| $H_2O_2$ plus MPO | 0.20 |

$^a$Values are mM concentrations of oxidants that produce 50% killing (the smaller the value, the more lethal the oxidant).
Abbreviations are: $LD_{50}$, lethal dose that causes 50% death; $H_2O_2$, hydrogen peroxide; HOCl, hypochlorous acid, HOOAc, peracetic acid; CPO, chloroperoxidase; MPO, myeloperoxidase.

While it is clear that these reaction products have potent antifungal and antimicrobial effects, the definitive mechanism of action of the antipathogenic effects of CPO-P in CPO-P-expressing transgenic plants have not as yet been determined. However, even though the exact mechanism of action involved in CPO-P-induced *A. flavus* lethality is not known, that at least two types of reaction products (hypohalites and peracetic acid) are present, is known. Furthermore, these two chemically different reaction products would be expected to react with different sites in a given bacteria or fungus, for example in *A. flavus*. Thus, an additional advantage of expressing a metal-free nonheme chloroperoxidase such as CPO-P is that the probability of a given pathogen developing resistance to the effects of the expressed CPO-P would be expected to be low. The combined probability of a fungus, e.g., *A. flavus*, developing resistance to the hypohalite together with the probability of its developing resistance to peracetic acid would be considered a rare event. However, the chances of developing resistance to hypohalite or peracetic acid, individually, would be expected to be slight to begin with, because each is a simple, powerful oxidant.

In a preferred embodiment of the present invention, the nucleic acid encoding a metal-free nonheme haloperoxidase gene, which is used to make the recombinant pathogen-resistant transgenic plant, is selected from the group consisting of: (a) an isolated DNA encoding a nonheme haloperoxidase; (b) an isolated DNA which hybridizes to isolated DNA of (a) above and which encodes a nonheme haloperoxidase protein or a peptide having nonheme haloperoxidase biological activity; and (c) an isolated DNA differing from the isolated DNAs of (a) and (b) above in nucleotide sequence due to the degeneracy of the genetic code, and which encodes a nonheme haloperoxidase protein or a peptide having nonheme haloperoxidase biological activity. "DNA which hybridizes to isolated DNA" refers to DNA sequences that can be identified in a Southern hybridization experiment under stringent conditions as is known in the art. See, for example, Sambrook et al. 1989. Molecular Cloning: A Laboratory Manual, Second Edition, Cold Spring Harbor Laboratory Press, Cold Spring Harbor, N.Y.

In a particularly preferred embodiment of the present invention, the nucleic acid encoding a metal-free nonheme haloperoxidase gene is a nonheme chloroperoxidase gene selected from the group consisting of: (a) an isolated DNA encoding a nonheme chloroperoxidase; (b) an isolated DNA which hybridizes to isolated DNA of (a) above and which encodes a nonheme chloroperoxidase protein or a peptide having nonheme chloroperoxidase biological activity; and (c) an isolated DNA differing from the isolated DNAs of (a) and (b) above in nucleotide sequence due to the degeneracy of the genetic code, and which encodes a nonheme chloroperoxidase protein or a peptide having nonheme chloroperoxidase biological activity.

In the most particularly preferred embodiment of the present invention, the nucleic acid encoding a nonheme chloroperoxidase gene is the CPO-P gene having the sequence identified by SEQ ID NO:1 or a portion thereof having nonheme chloroperoxidase biological activity.

In a further embodiment of the present invention, said DNA is a recombinant chimeric gene construct comprising a promoter operable in a plant cell and a DNA encoding the nonheme haloperoxidase, or preferably the nonheme chloroperoxidase, described above. In another embodiment, the chimeric gene construct additionally encodes at least one selectable marker and/or further comprises a heterologous coding sequence, wherein the heterologous coding sequence is an isolated DNA encoding a polypeptide sequence having a property which is advantageous to the plant and which is different from the nonheme haloperoxidase or chloroperoxidase. Genes encoding polypeptides having properties advantageous to the plant and anti-phytopathogenic polypeptides are well known in the art. Examples include genes which encode proteins which protect plants against pathogens, herbicides, fungicides, insecticides, or disadvantageous environmental influences, wherein the disadvantageous environmental influences comprise heat, cold, wind, unfavorable soil conditions, moisture and dryness.

In a still further preferred embodiment of the present invention, said recombinant chimeric gene construct further comprises DNA encoding a 5' untranslated region containing a translational enhancer and DNA encoding a 3' untranslated region containing a functional polyadenylation signal or parts of these regulatory elements.

In another preferred embodiment of the present invention, the DNA sequence encoding the protein or peptide having nonheme chloroperoxidase activity or the DNA sequence comprising the heterologous coding sequence is derived from a mammalian gene, a plant gene or a microorganism gene or is a synthetic gene.

In a preferred embodiment of the present invention said DNA is contained in a vector under the control of a promoter allowing its expression in said transgenic plant. Further embodiments of the invention include plant cells transformed by these vectors, plant parts, and plants and their progeny containing the chimeric genes.

In a particularly preferred embodiment of the present invention said vector is KYLX7.1.

In a preferred embodiment of the present invention, a host cell containing the DNA of the invention is a bacterial cell, in particular, an *Agrobacterium tumefaciens* cell.

In a preferred embodiment of the present invention, the protein encoded by said DNA sequence is a nonheme chloroperoxidase. In a particularly preferred embodiment of the present invention, said chloroperoxidase is a metal-free nonheme chloroperoxidase from *Pseudomonas pyrrocinia*, CPO-P identified by SEQ ID NO:2.

As used herein, the term "chimeric" refers to two or more DNA molecules which are derived from different sources, strains, or species, which do not recombine under natural conditions, or to two or more DNA molecules from the same species, which are linked in a manner that does not occur in the native genome. Thus, the present constructs and vectors permit the augmentation of plant genomes with a limited number of preselected genes. As used herein, "recombinant" refers to a nucleic acid molecule which has been obtained by manipulation of genetic material using restriction enzymes, ligases, and similar recombinant techniques as described by, for example, Sambrook et al., supra. "Recombinant," as used herein, does not refer to naturally occurring genetic recombinations. As used herein, the term "express" or "expression" is defined to mean transcription alone. The regulatory elements are operably linked to the coding sequence of the metal-free nonheme haloperoxidase gene such that the regulatory element is capable of controlling expression of the metal-free nonheme haloperoxidase gene. "Heterologous coding sequence" refers to coding sequences which encode peptides or proteins, unrelated to, or, other than, the metal-free nonheme haloperoxidase provided above and which are not intrinsically found in the position provided in the chimeric gene construct, i.e., DNA coding sequences which are derived from different sources, strains, or species, which do not recombine under natural conditions, or to two or more DNA coding sequences from the same species, which are linked in a manner that does not occur in the native genome.

Genes encoding a nonheme haloperoxidase, e.g., a chloroperoxidase can be cloned using a variety of techniques according to the invention. The simplest procedure for the cloning of chloroperoxidase genes requires the cloning of genomic DNA from an organism identified as producing chloroperoxidase, and the transfer of the cloned DNA on a suitable plasmid or vector to a host organism which does not produce chloroperoxidase, followed by the identification of transformed host colonies to which the ability to produce chloroperoxidase has been conferred. The transforming chloroperoxidase-conferring DNA can be cleaved into smaller fragments and the smallest which maintains the chloroperoxidase-conferring ability can be further characterized. Chloroperoxidase biosynthetic genes which are required for the synthesis of chloroperoxidase and which are similar to known chloroperoxidase compounds may be clonable by virtue of their sequence homology to the biosynthetic genes of the known compounds. Techniques suitable for cloning by homology include standard library screening by DNA hybridization. As defined herein, two DNA sequences are substantially homologous when at least 85% (preferably at least 90% and most preferably 95%) of the nucleotides match over the defined length of the sequence using algorithms such as CLUSTRAL or PILEUP. Sequences that are substantially homologous can be identified in a Southern hybridization experiment under stringent conditions as is known in the art. See, for example, Sambrook et al., supra, or DNA Cloning: A Practical Approach, Vol. I and II (Ed. D. N. Glover), IRL Press, Oxford, 1985. Sambrook et al. describe highly stringent conditions as a hybridization temperature 5–10° C. below the $T_m$ of a perfectly matched target and probe; thus, sequences that are "substantially homologous" would hybridize under such conditions.

Another embodiment of this invention is the method of making a recombinant pathogen-resistant plant, said method comprising: providing a plant cell capable of regeneration; transforming said plant cell with a DNA segment encoding a haloperoxidase, where said DNA segment is selected from the group consisting of: (a) an isolated DNA encoding a nonheme haloperoxidase; (b) an isolated DNA which hybridizes to isolated DNA of (a) above and which encodes a nonheme haloperoxidase protein or a peptide having nonheme haloperoxidase biological activity; and (c) an isolated DNA differing from the isolated DNAs of (a) and (b) above in nucleotide sequence due to the degeneracy of the genetic code, and which encode a nonheme haloperoxidase protein or a peptide having nonheme haloperoxidase biological activity; and then regenerating a recombinant pathogen-resistant plant from said transformed plant cell.

Still another embodiment of this invention is the method of making a recombinant pathogen-resistant plant, said method comprising: providing a plant cell capable of regeneration; transforming said plant cell with a DNA segment encoding a chloroperoxidase, where said DNA segment is selected from the group consisting of: (a) an isolated DNA encoding a nonheme chloroperoxidase; (b) an isolated DNA which hybridizes to isolated DNA of (a) above and which encodes a nonheme chloroperoxidase protein or a peptide having nonheme chloroperoxidase biological activity; and (c) an isolated DNA differing from the isolated DNAs of (a) and (b) above in nucleotide sequence due to the degeneracy of the genetic code, and which encode a nonheme chloroperoxidase protein or a peptide having nonheme chloroperoxidase biological activity; and then regenerating a recombinant pathogen-resistant plant from said transformed plant cell.

Yet another embodiment of this invention is the method of making a recombinant pathogen-resistant plant, said method comprising: providing a plant cell capable of regeneration; transforming said plant cell with the chimeric gene construct comprising a promoter operable in said plant cell, and a DNA segment encoding a haloperoxidase, where said DNA segment is selected from the group consisting of: (a) an isolated DNA encoding a nonheme haloperoxidase; (b) an isolated DNA which hybridizes to isolated DNA of (a) above and which encodes a nonheme haloperoxidase protein or a peptide having nonheme haloperoxidase biological activity; and (c) an isolated DNA differing from the isolated DNAs of (a) and (b) above in nucleotide sequence due to the degeneracy of the genetic code, and which encode a nonheme haloperoxidase protein or a peptide having nonheme haloperoxidase biological activity; and then regenerating a recombinant pathogen-resistant plant from said transformed plant cell.

A preferred embodiment of this invention is the method of making a recombinant pathogen-resistant plant, said method comprising: providing a plant cell capable of regeneration; transforming said plant cell with a chimeric gene construct comprising a promoter operable in said plant cell, and a DNA segment encoding a chloroperoxidase, where said DNA segment is selected from the group consisting of: (a) an isolated DNA encoding a nonheme chloroperoxidase; (b) an isolated DNA which hybridizes to isolated DNA of (a) above and which encodes a nonheme chloroperoxidase protein or a peptide having nonheme chloroperoxidase biological activity; and (c) an isolated DNA differing from the isolated DNAs of (a) and (b) above in nucleotide sequence due to the degeneracy of the genetic code, and which encode a nonheme chloroperoxidase protein or a peptide having nonheme chloroperoxidase biological activity; and then regenerating a recombinant pathogen-resistant plant from said transformed plant cell.

A further embodiment of the present invention is a method for the production of a transgenic plant displaying resistance to phytopathogens comprising the introduction of a genetically engineered DNA sequence encoding at least one peptide having chloroperoxidase activity, into the genetic material of a suitable plant. The term "genetic material" refers to the nuclear genome of a plant cell, an organelle genome of the plant cell or an extrachromosomal form. The term "introduction" refers to a method which is capable of introducing said genetically engineered DNA sequence into said genetic material of a plant cell. Preferred examples of said method are Agrobacterium-mediated transfer, plant virus mediated-transfer, microinjection, microprojectile bombardment, electroporation, PEG-mediated transformation and transformation of plant protoplasts with virus-based stable vectors, all methods well known and practiced in the art. In a further preferred embodiment of the present invention said introduction is carried out by transfection using the Agrobacterium system.

It is yet another embodiment of the invention to provide methods for the manipulation of chloroperoxidase gene sequences for their expression in transgenic plants, both monocotyledoneous or dicotyledoneous plants. In a preferred embodiment of the present invention the transgenic plant is cotton, maize, peanut, sunflower, tobacco, rice, wheat, rye, barley, alfalfa, tomato, cucumber, soya, sweet potato, grapes, rapeseed, sugar beet, tea, strawberry, rose, chrysanthemum, poplar, eggplant, sweet pepper, walnut, pistachio, mango, banana, or potato. In a particularly preferred embodiment of the invention, chloroperoxidase is expressed in *Gossypium hirsutum* and *Nicotiana tabacum* cvs. Xanthi and SR-1. The transgenic plants thus modified have enhanced resistance to attack by phytopathogens.

The genes for chloroperoxidase of this invention are expressed in transgenic plants thus causing the biosynthesis of chloroperoxidase in the transgenic plants. In this way transgenic plants with enhanced resistance to phytopathogenic fungi and bacteria are generated. For their optimal expression in transgenic plants, the chloroperoxidase genes and adjacent sequences may require modification and optimization.

Although in many cases genes from microbial organisms can be expressed in plants at high levels without modification, low expression in transgenic plants may result from chloroperoxidase genes having codons which are not preferred in plants. It is known in the art and summarized, for example, in U.S. Pat. No. 5,817,502 herein incorporated by reference, that all organisms have specific preferences for codon usage, and the chloroperoxidase gene codons can be changed to conform with plant preferences, while maintaining the amino acids encoded. Furthermore, high expression in plants is best achieved from coding sequences which have at least 35% GC content, and preferably more than 45%. Microbial genes which have low GC contents may express poorly in plants due to the existence of ATTTA motifs which may destabilize messages, and AATAAA motifs which may cause inappropriate polyadenylation. In addition, potential chloroperoxidase biosynthetic genes can be screened for the existence of illegitimate splice sites which may cause message truncation. All changes required to be made within the chloroperoxidase coding sequence such as those described above can be made using well known techniques of site directed mutagenesis, PCR, and synthetic gene construction using methods well known in the art. The preferred chloroperoxidase biosynthetic genes may be unmodified genes, should these be expressed at high levels in target transgenic plant species, or alternatively may be genes modified by the removal of destabilization and inappropriate polyadenylation motifs and illegitimate splice sites, and further modified by the incorporation of plant preferred codons, and further with a GC content preferred for expression in plants. Although preferred gene sequences may be adequately expressed in both monocotyledonous and dicotyledonous plant species, sequences can be modified to account for the specific codon preferences and GC content preferences of monocotyledons or dicotyledons as these preferences have been shown to differ (Murray et al. 1989. *Nucl. Acid Res.* 17: 477–498).

For efficient initiation of translation, sequences adjacent to the initiating methionine may require modification. The sequences cognate to the selected chloroperoxidase genes may initiate translation efficiently in plants, or alternatively may do so inefficiently. In the case that they do so inefficiently, they can be modified by the inclusion of sequences known to be effective in plants. Joshi has suggested an appropriate consensus for plants (1987. *Nucl. Acid Res.* 15: 6643–6653) and Clontech suggests a further consensus translation initiator (1993/1994 catalog, page 210). These consensuses are suitable for use with the chloroperoxidase biosynthetic genes of this invention. The sequences are incorporated into the chloroperoxidase gene construction, up to and including the ATG (whilst leaving the second amino acid of the chloroperoxidase gene unmodified), or alternatively up to and including the GTC subsequent to the ATG (with the possibility of modifying the second amino acid of the transgene).

Transgenic plants can be transformed with a DNA segment encoding a haloperoxidase in the absence of an exogenously provided promoter. However, when chimeric gene constructs comprising a promoter operable in said plant cell and a DNA segment encoding a haloperoxidase are utilized for the transformation, optimal expression of haloperoxidase results. The expression of chloroperoxidase genes in transgenic plants is behind a promoter shown to be functional in plants. The choice of promoter will vary depending on the temporal and spatial requirements for expression, and also depending on the target tissue or species. The expression of chloroperoxidase genes in transgenic plants can be under the regulation of promoters which are constitutive or promoters which are regulated. Such promoters are well known in the art and described, for example, in U.S. Pat. No. 5,589,625; examples are: cauliflower mosaic virus 35S-promoter, rice actin promoter, rbc S promoter from different species, Agrobacter TR2' promoter, phaseolin gene promoter or the NOS promoter. Preferred promoters which are expressed constitutively include CaMV 35S, the cauliflower mosaic virus 35S-promoter, and 19S promoters, and promoters from genes encoding actin or ubiquitin. Constitutive expression of chloroperoxidase CPO-P under the control of the cauliflower mosaic virus 35S-promoter is preferred. In transgenic plants, like non-transgenic plants, attack by fungal and microbial pathogens results in a respiratory burst where hydrogen peroxide is generated. Thus, transgenic plants transformed with a chimeric gene construct comprising a constitutively-regulated promoter is capable of an immediate response without further induction.

The expression of the chloroperoxidase genes of this invention can also be controlled, i.e., under the regulation of promoters which are regulated. Thus, this transformation method can be developed to control disease in particular crops. An advantage of controlled expression of the chimeric gene construct is that chloroperoxidase is expressed only at the appropriate time and/or to the appropriate extent and/or only in particular parts of the plant. A further advantage is that parts of plants that are inaccessible to conventional protective measures, can be protected using this method either through constitutive expression of the nucleic acid in all tissues or through tissue-specific expression of the nucleic acid as controlled by tissue or stage-specific promoters. Furthermore, this transformation method to control disease and these transgenic plants can be further developed to where expression of the gene occurs under particular circumstances, e.g., wounding, drought, and chemical induction.

For example, the problem of fungal contamination of crops increases after a drought period. In response to such a situation, very high levels of chloroperoxidase expression may be desirable. To offset the increased energy required to generate high levels of the chloroperoxidase constitutively, a strategy to regulate chloroperoxidase expression when needed would be to engineer a drought-inducible promoter into the chimeric gene construct expressed by the transgenic plant so that the chloroperoxidase gene is expressed only when a fungal infestation is imminent. Similarly, the use of promoters which are chemically regulated enables chloroperoxidase to be synthesized only when the crop plants are treated with the inducing chemicals. Further, the chloroperoxidase genes of this invention can be expressed under the regulation of promoters which are wound inducible. Numerous promoters have been described which are expressed at wound sites and also at the sites of phytopathogen infection. These are suitable for the expression of chloroperoxidase genes because chloroperoxidase biosynthesis is turned on by phytopathogen infection and thus the chloroperoxidase only accumulates when infection occurs. Ideally, such a promoter should only be active locally at the sites of infection, and in this way chloroperoxidase only accumulates in cells which need to synthesize the chloroperoxidase to kill the invading phytopathogen. Preferred promoters of this kind include those described by Stanford et al. 1989. *Mol. Gen. Genet.* 215: 200–208, Xu et al. 1993. *Plant Molec. Biol.* 22: 573–588, Logemann et al. 1989. *Plant Cell* 1: 151–158, Rohrmeier et al. 1993. *Plant Molec. Biol.* 22: 783–792, Firek et al. 1993. *Plant Molec. Biol.* 22: 129–142, and Warner et al. 1993. *Plant J.* 3: 191–201.

Examples of tissue specific expression patterns include fiber specific, green tissue specific, root specific, stem specific, and flower specific. For the protection of plants against foliar pathogens, expression in leaves is preferred; for the protection of plants against ear pathogens, expression in inflorescences (e.g. spikes, panicles, cobs etc.) is preferred; for protection of plants against root pathogens, expression in roots is preferred; for protection of seedlings against soil-borne pathogens, expression in roots and/or seedlings is preferred. In many cases, however, protection against more than one type of phytopathogen will be sought, and thus expression in multiple tissues will be desirable. Although many promoters from dicotyledons have been shown to be operational in monocotyledons and vice versa, ideally dicotyledonous promoters are selected for expression in dicotyledons, and monocotyledonous promoters for expression in monocotyledons. However, there is no restriction to the provenance of selected promoters; it is sufficient that they are operational in driving the expression of the chloroperoxidase biosynthetic genes. Promoters suitable for expression in green tissue include many which regulate genes involved in photosynthesis and many of these have been cloned from both monocotyledons and dicotyledons. A preferred promoter is the maize PEPC promoter from the phosphenol carboxylase gene (Hudspeth et al. 1989. *Plant Molec. Biol.* 12: 579–589). A preferred promoter for root specific expression is that described by de Framond (1991. *FEBS* 290: 103–106) or by Hudspeth et al. (1996. *Plant Molec. Biol.* 31: 701–705). A preferred stem specific promoter is that described in patent application WO 93/07278 (to Ciba-Geigy) and which drives expression of the maize trpA gene.

In addition to the selection of a suitable promoter, constructions for chloroperoxidase expression in plants require an appropriate transcription terminator to be attached downstream of the heterologous chloroperoxidase gene. Several such terminators are available and known in the art (e.g. tml from CaMV, E9 from rbcS). Any available terminator known to function in plants can be used in the context of this invention.

Numerous other sequences can be incorporated into expression cassettes for chloroperoxidase genes. These include sequences which have been shown to enhance expression such as intron sequences (e.g. from Adhl and bronzel) and viral leader sequences (e.g. from TMV, MCMV and AMV).

In some situations, the overexpression of chloroperoxidase gene may deplete the cellular availability of the substrate for a particular pathway and this may have detrimental effects on the cell. Solutions to this type of problem are known and practiced in the art. For example, genes which encode the enzymes for the biosynthesis of the substrate can be overexpressed resulting in an increased amount of substrate or it may be possible to turn off known pathways which utilize specific substrates without detrimental side effects.

For Agrobacterium-mediated transformation, binary vectors or vectors carrying at least one T-DNA border sequence are suitable, whereas for direct gene transfer any vector is suitable and linear DNA containing only the construction of interest may be preferred. In the case of direct gene transfer, transformation with a single DNA species or co-transformation can be used (Schocher et al. 1986. *Biotechnology* 4: 1093–1096). For both direct gene transfer and Agrobacterium-mediated transfer, transformation is usually (but not necessarily) undertaken with a selectable marker which may provide resistance to an antibiotic (kanamycin, hygromycin or methatrexate) or a herbicide (sulfonylurea, imidazolinone, or basta). The choice of selectable marker is not, however, critical to the invention.

The present invention also relates to methods of treating plants, which comprise application of antifungal compositions to plants wherein the antifungal composition is plant material from the transgenic plants of the invention, i.e., plants expressing a nonheme haloperoxidase, or extracts of such transgenic plant material. The active ingredients of the present invention are normally applied in the form of compositions and can be applied to the crop area or plant to be treated, simultaneously or in succession, with further compounds as is known and practiced in the art, e.g., fertilizers, selective herbicides, insecticides, fungicides, bactericides, nematicides, molluscicides or mixtures of several of these preparations, if desired together with further carriers, surfactants or application-promoting adjuvants customarily employed in the art of formulation. The crops or plants to be treated can be transgenic plants or crops or non-transformed plants or crops. The active ingredients may also be applied to seeds (coating) by impregnating the seeds either with a liquid formulation containing active ingredients, or coating them with a solid formulation. In some cases, expression of chloroperoxidase in plants may provide protection against insect pests.

Another embodiment of the invention relates to DNA primers from the sequence described in SEQ ID NO:1. The invention comprises a method for specifically identifying the chloroperoxidase CPO-P which comprises amplifying a subject mRNA by the RT-PCR method with the use of the above-mentioned DNA primers and thus assaying the expression of the CPO-P gene.

An additional embodiment of the invention relates to peptides which have metal-free nonheme chloroperoxidase activity which can be used to generate antibodies. Such antibodies can be used to detect the presence a peptide having nonheme chloroperoxidase biological activity in biological samples.

EXAMPLES

The following examples serve as further description of the invention and methods for practicing the invention. They are not intended as being limiting, rather as providing guidelines on how the invention may be practiced. Further explanations of the molecular biological methods applied can be found in Sambrook et al., supra.

Example 1

Cloning and Manipulations

Total genomic DNA was isolated from tobacco leaf tissue using the method of Paterson et al. (1993. *Plant. Mol. Biol. Rep.* 11: 122–127). Total RNA was isolated from leaf material according to the method of Logemann et al. (1987. *Anal. Biochem.* 163: 16–20). The cpo gene from *P. pyrrocinia* (SEQ ID NO:1) was subcloned into the plant binary vector KYLX 7.1 which places expression of the gene under the control of the CaMV 35S promoter (Schardl et al. 1987. *Gene* 61: 1–11). Synthetic oligonucleotide primers were designed for amplification of the cpo ORF based on N-terminal and C-terminal sequence data. The primers had HindIII (CPO-N) and SacI (CPO-C) restriction enzyme sites engineered into them to facilitate subcloning into the binary vector. Using plasmid pHW321 (Wolfframm et al., supra) harboring the cpo gene as template, the primers CPO-N, 5'-AAGCTTTGCCATACGTCACTACG-3' (SEQ ID NO:3) and CPO-C, 5'-GAGCTCTACGCCTGCACGAACG-3' (SEQ ID NO:4) were used to amplify the cpo coding region using Pfu polymerase (Stratagene, La Jolla, Calif.). The 836 bp PCR product was subcloned into vector pCRScript-Cm (Stratagene) and sequenced to confirm fidelity of the PCR reaction. The cpo coding region was released from pCRScript-CPO DNA by HindIII-SacI digestion and subcloned into HindIII-SacI digested KYLX 7.1 vector DNA (Schardl et al., supra). The resulting vector, KYLX-cpo was transformed into electrocompetent *Agrobacterium tumefaciens* LBA 4404 cells (Gibco-BRL, Bethesda, Md.) via electroporation using a Bio-Rad Cell-Porator (Bio-Rad, Hercules, Calif.) according to the manufacturer's procedure.

Example 2

Plant Transformation

Transformation of tobacco (*Nicotiana tabacum* cvs. Xanthi and SR-1) was accomplished using the *A. tumefaciens*-mediated leaf disk transformation system (Horsch et al. 1985. *Science* 227: 1229–1231. The selection of MS medium (Murashige et al. 1962. *Physiol. Plant* 15: 473–497) supplemented with 6-benzylaminopurine (0.75 mg/l) also included kanamycin (200 mg/l) for selection of transformed cells. The kanamycin-tolerant shoot buds were transferred to MS medium containing kanamycin (50 mg/l) and the rooted plants were subsequently transferred to soil for further evaluation in a growth chamber (28° C., 16 h d). The potted plants were also assayed for the presence of neomycin phosphotransferase II (NPTII) protein by ELISA (Rajasekaran et al. 1996. *Mol. Breed.* 2: 307–319). Plants regenerated from a parallel transformation experiment with pBI121 served as negative controls in the molecular and antifungal analyses.

Each leaf disk produced at least five transformed shoots in the presence of toxic levels of kanamycin (200 mg/l), which developed roots in growth media containing inhibitory levels of kanamycin (50 mg/l). The putative antibiotic-resistant plantlets were assayed for the presence of NPTII. To obtain different individual transformants only one NPTII-positive plantlet from each leaf disk was transferred to the greenhouse. All of the ten transgenic tobacco plants of cv. Xanthi carrying the cpo gene were morphologically similar to non-transformed controls with respect to flowering and seed set. Six $R_0$ plants, labeled H1, H2, H3, H5, H6, and H7, were utilized in the disease resistance assays. Using a different variety (SR-1), the transformation and the disease resistance assays were duplicated with a second set of ten $R_0$ transformants with similar results (data not shown).

Example 3

PCR and Southern Blot Analysis of Plant Genomic DNA

To determine if the CaMV 35S-cpo T-DNA region had successfully integrated into the plant genome, a 640 bp region spanning from within the CAMV 35S promoter to 400 bp into the cpo gene was PCR amplified from total plant genomic DNA. The CaMV 35S primer, 5'-TCATTGCGATAAAGGAAAGGCC-3' (SEQ ID NO:5) and the CPO internal primer, 5'-GATTCGGTTTTCAGCATCAGC-3' (SEQ ID NO:6) were used to amplify plant genomic DNA using AmpliTaq polymerase (Stratagene). Thermocycler (MJ Research, Watertown, Mass.) parameters were as follows: 1 cycle of 95° C., 5 min; 58° C., 1 min; 72° C., 30s; 1 cycle of 95° C., 1 min; 60° C., 1 min; 72° C., 30 s; 32 cycles of 95° C., 1 min; 65° C., 1 min; 72° C., 30 s. This was followed by a final extension of 72° C. for 1 min. PCR products were analyzed by electrophoresis on a 1% agarose gel followed by ethidium bromide staining.

For southern blot analysis, tobacco genomic DNA (20 $\mu$g) was digested to completion with EcoRI and electrophoresed on a 1% agarose gel. DNA was transferred to nylon membranes (Schleicher & Schuell, Keene, N.H.) by vacuum transfer and hybridized with the 836 bp random-primed, $^{32}P$-labeled, cpo gene PCR product.

Figure 2:
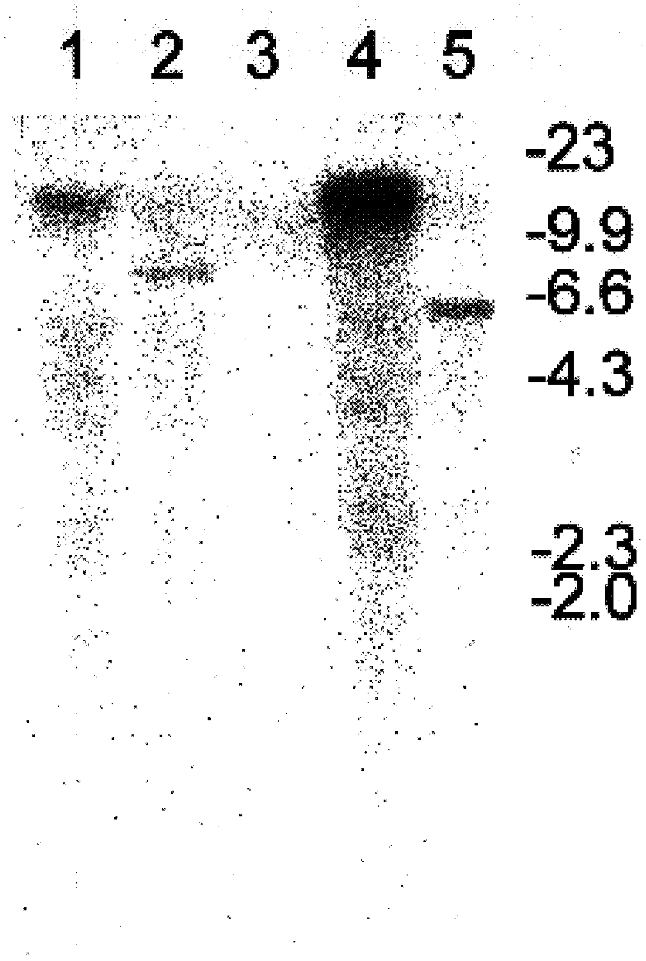
FIG. 2 shows a southern hybridization of tobacco genomic DNA with a radiolabeled cpo gene probe. Tobacco genomic DNA (20 μg) was digested to completion with EcoRI, electrophoresed, blotted to nylon membrane, and hybridized with the $^{32}P$-labeled 836 bp cpo gene PCR probe. Lanes: 1, H1; 2, H2; 3, negative control plant transformed with pBI121; 4, H5; 5, H7. HindIII-digested lambda DNA (in kbp) was used as molecular size standard.

Agarose gel electrophoresis of PCR products from the transgenic plant samples showed the expected PCR product of 640 bp representing the region of DNA spanning from within the CaMV 35S promoter to 400 bp into the cpo gene (FIG. 1). The no-DNA sample and negative control DNA from pBI121 transformed sample did not show this product. Southern transfer of the PCR samples and hybridization with the radiolabeled cpo gene probe demonstrated a band of hybridization at about 640 bp, confirming that the PCR product did represent the CAMV 35S-cpo gene region in all the putative transgenic plants (FIG. 1). No signal was detected in the no-DNA or negative tobacco DNA control lanes. Southern blot analysis of EcoRI-digested plant genomic DNA from H1, H2, H5, and H7 showed that all the transgenic plant tissues gave a single hybridization signal with the radiolabeled cpo gene probe (FIG. 2). The pBI121-transformed control lane did not show a hybridization signal with the probe, as expected. The length of the fragment from the T-DNA insertion site to the closest EcoR1 of the surrounding plant DNA was approximately the same for H1 and H5 (FIG. 2).

With the possible exception of plant H5, all of the other transformed plants appeared to have only one copy of the cpo gene integrated into the plant genome. The intensity of the signal in plant H5 DNA is possibly due to loading of more DNA, as confirmed by ethidium bromide staining prior to Southern transfer.

Example 4

Northern Blot Analysis of cpo Transcripts

Total plant RNA was isolated and electrophoresed on a 2.2 M formaldehyde/agarose gel according to standard methods (Ausubel et al. 1993. Current Protocols in Molecular Biology. J. Wiley, New York, N.Y.). RNA was transferred to a nylon membrane by vacuum transfer and hybridized with the 836 bp $^{32}P$-labeled, cpo gene PCR product.

Figure 3A:
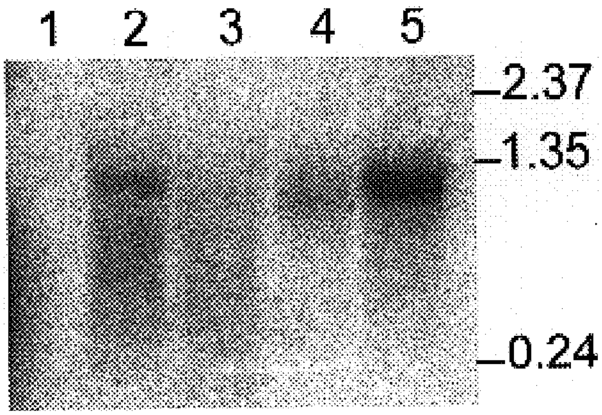
FIG. 3A shows a northern hybridization analysis of transcripts probed with radiolabeled cpo gene. Total RNA (10 μg) was separated electrophorectically, blotted, and hybridized with the $^{32}P$-labeled 836 bp cpo gene PCR probe. Lanes: 1, tobacco negative control plant transformed with pBI121; 2, H1; 3, H2; 4, H5; 5, H7. The position of molecular size markers (in kb) is shown.
Figure 3B:
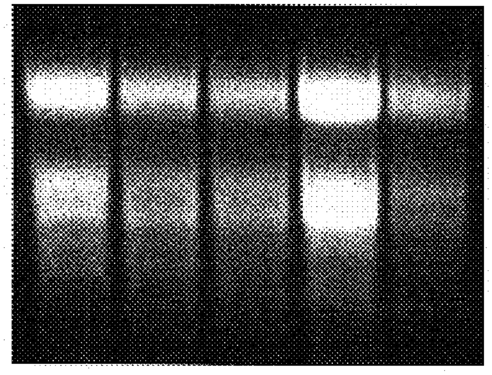
FIG. 3B shows RNA stained with ethidium bromide to indicate the amount loaded.

Hybridization of total RNA with the radiolabeled cpo gene ORF fragment demonstrated the presence of cpo transcripts in all samples tested except the negative control (FIG. 3). Highest transcript levels were observed with sample H7 followed by sample H1. Very little cpo transcript was detected in samples H2 and H5 and this was apparently due to degradation of the cpo mRNA, as a significant amount of smearing of the signal was observed.

Example 5

Western Blot Analysis of cpo Expression

Plant leaf tissue was ground to a fine powder with liquid nitrogen in the presence of an extraction buffer (62.5 mM Tris-HCl, pH 6.8; 2% SDS; 10% glycerol; 5% 2-mercaptoethanol). Cell debris was removed by centrifugation at 13,000 g at room temperature for 5 min. Supernatant was collected and the total protein in each sample was determined using the Bio-Rad Protein Assay kit (BioRad) with bovine serum albumin as a standard. Bromophenol blue (0.05%) was added to the protein samples which were then separated on a 10% polyacrylamide gel along with protein molecular weight standards (14.4-200 kDa Rainbow Markers, Amersham International, Amersham, UK). Following electrophoresis, the proteins were transferred to PBDF membranes (ICN, Costa Mesa, Calif.) using a Semi-Phor electroblotter (Hoefer Scientific, San Francisco, Calif.). CPO-P protein was detected using BioRad immunodetection procedures with CPO-P polyclonal anti-serum (1:200 dilution) and goat anti-rabbit, alkaline phosphatase secondary antibody conjugate (BioRad, 1:3000 dilution). Nitro-blue terazolium and 5-bromo-4-chloro-3-indolylphosphate reagents were used for color development.

Figure 4:
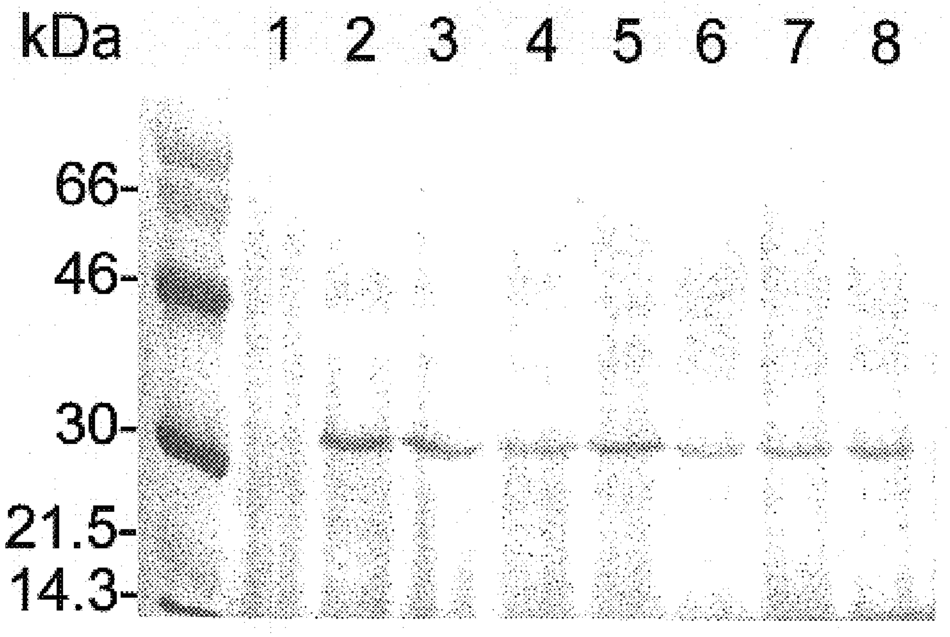
FIG. 4 shows a western blot analysis of CPO-P protein from tobacco tissue. Crude protein extracts of tobacco leaf tissue were separated on a 10% SDS-polyacrylamide gel and electroblotted to PVDF membrane. The membrane was treated with a 1:200 dilution of CPO-P polyclonal antiserum. Lanes: 1, negative control plant transformed with pBI121; 2, H1; 3, H2; 4, H3; 5, negative control plant sample with 10 ng pure CPO-P protein added; 6, H5; 7, H6; 8, H7. Molecular weight standards (in kDa) are shown.

All transgenic plant samples demonstrated a band of reactivity at approximately 31 kDa (FIG. 4). This band aligned exactly with the protein sample from the negative control plant transformed with pBI121 that had 10 ng of purified cpo protein added to it.

Example 6

Evaluation of CPO-P Enzyme Activity in Transgenic Leaf Extracts

Young expanding leaves were pulverized in liquid $N_2$ with two parts (v/w) of 1.0 M Na acetate buffer (pH 5.5) and centrifuged at 15,000 g for 10 min. Then 0.1 part (w/v) of insoluble, high MW, cross-linked polyvinylpyrrolidone was added to the liquid supernatant and the mixture was centrifuged again at 15,000 g for 10 min. The supernatant was assayed for halogenating activities.

Halogenating activity of CPO-P in leaf extracts was assayed with 0.8M Na acetate buffer, pH 5.5, containing 44 $\mu$M monochlorodimedon (MCD), 7.2 mM $H_2O_2$, 82 mM NaBr, and 8.9 mM $NaN_3$ (Picard et al., supra). The reaction was initiated by the addition of leaf extract and the decrease in absorbance at 290 nm due to halogenation of MCD was monitored.

Halogenating activity of CPO-P was observed in transgenic tobacco plants but not in the negative control plants (Table 2).

TABLE 2

CPO—P Activity in Transformed and Non-transformed Tobacco (cv. Xanthi).

| Leaf Source | Units of enzyme/g of tissue[a] |
|---|---|
| Control - Transformed with pBl121 | 0 |
| Transgenic - Transformed with CPO—P | |
| H1 | 4.7 |
| H2 | 11.3 |
| H3 | 2.5 |
| H5 | 1.9 |
| H6 | 5.8 |
| H7 | 10.4 |

[a]One unit of enzyme is defined as the amount that catalyzes the formation of 1 millimole monochloro-monobromodimedon/hour. Values are averages of three determinations; ranges were within 5% of the averages.

Figure 5A:
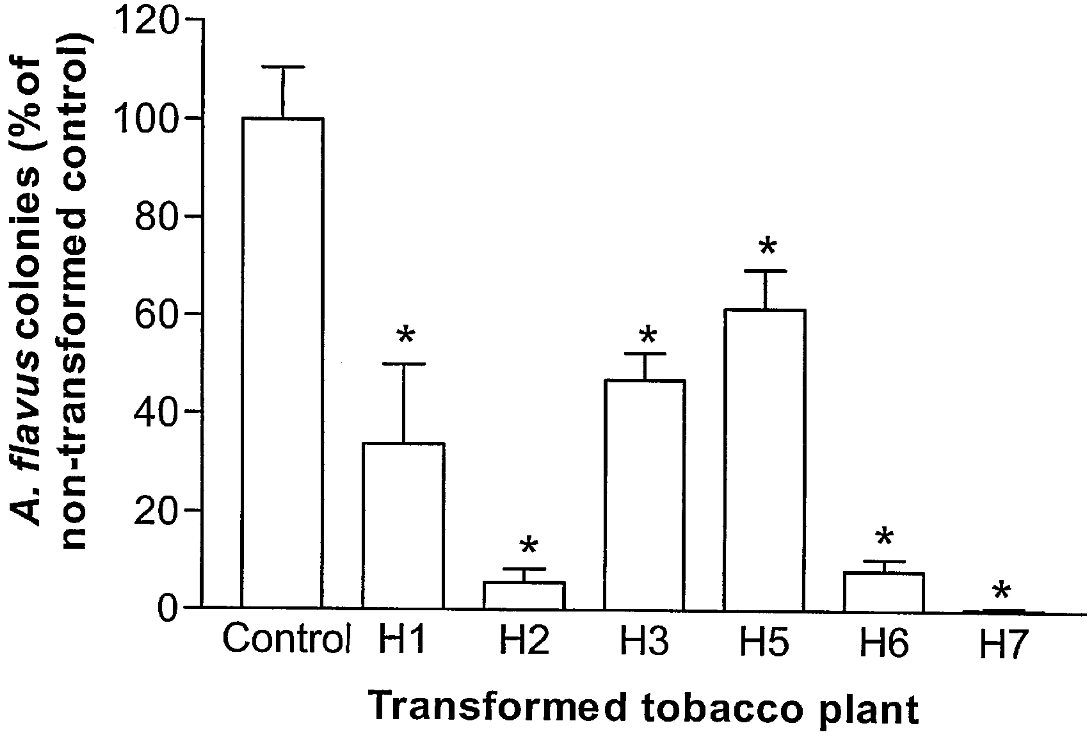
FIG. 5A shows inhibition of germinated spores of *Aspergillus flavus* by leaf extracts from tobacco plants transformed with the cpo gene construct compared with the negative control (C). Asterisk (*) denotes significant reduction (P<0.05) in the number of *A. flavus* colonies compared with control plants transformed with pBI121. Mean values of at least two separate analyses, with a minimum of three replicates in each, are given. Error bars indicate standard error of means (SEM). Mean separation was performed by Tukey's method.

Plants shown to have increased enzymatic activity, above, have correspondingly increased antifungal activity when results listed in Table 2 for plants C and H1, H2, H3, H5, H6, H7 are compared to antifungal results for the same plants as described below in Example 7 and as shown in FIG. 5A.

The validity of the assay procedure for CPO-P activity in transgenic tobacco was established in the following manner. Complete recovery of enzymic activity was obtained in leaf extracts from negative control plants spiked with authentic CPO-P, which is consistent with physiological compatibility of the plant cellular milieu for CPO-P. Furthermore, $NaN_3$ completely inhibited endogenous peroxidase activity in leaf extracts as shown by assaying peroxidase with guaiacol (George, P. 1953. *J. Biol. Chem.* 201: 413–426). These results show that artifacts from endogenous peroxidases were absent and that only non-heme CPO-P activity was being measured.

Example 7

In Vitro Analysis of Antifungal Activity of Extracts of Transgenic Tobacco Plants The inhibitory activity of extracts from tobacco plants transformed with the cpo gene was assessed in vitro following the method of DeLucca et al. (1997. *Antimicrob. Agents Chemother.* 41: 481–483).

Plant homogenates were prepared by grinding tobacco leaves with liquid $N_2$ with no buffer added. Ground tissues were then centrifuged at 8200 g for 10 min at room temperature and extract collected from each sample. Control samples consisted of extract from tobacco plants transformed with pBI121. Pre-germinated conidial suspensions ($10^5$ conidia/ml) of *A. flavus* (25 $\mu$l) were then added to 225 $\mu$l of plant extract, mixed, and incubated for 60 min at 30° C. Three 50 $\mu$l aliquots from each sample tested were then spread onto potato dextrose-agar (PDA) plates and incubated at 30° C. for 24 h and fungal colonies enumerated. Antifungal assays were conducted at least three times. One-way ANOVA was used to determine the effect of extracts collected from transformed plants on germinating conidia. Mean separations were performed using the method of Tukey (Sokal et al. 1981. Biometry—The Principles and Practice of Statistics in Biological Research, Freeman, New York, N.Y.).

Figure 5B:
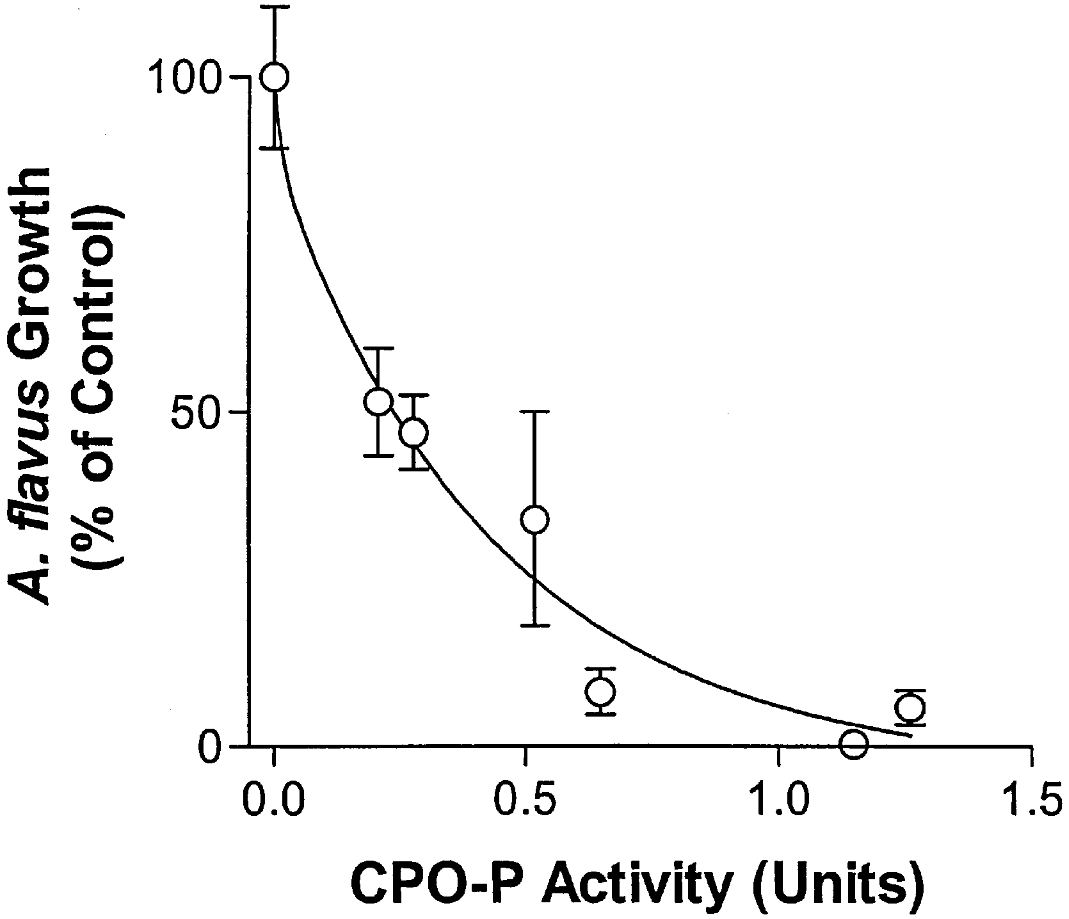
FIG. 5B shows the inhibition of *A. flavus* growth by leaf extracts as a function of CPO-P activity in tobacco leaves from transgenic plants. Vertical bars represent SEM (n=6).

Plant extracts from tobacco plants transformed with the cpo gene significantly reduced ($P<0.05$) the number of fungal colonies arising from germinating conidia of *A. flavus* compared with the extracts from the pBI121-transformed control (FIG. 5A). Extracts from the transformed plants reduced the number of *A. flavus* colonies by up to 100% compared with the negative tobacco control (FIG. 5A). The contents of CPO-P activity in transgenic tobacco leaves are thus correlated to their lethalities against *A. flavus* (FIG. 5B).

Example 8

In Planta Antifungal Assay for Tobacco Anthracnose Resistance

*Colletotrichum destructivum* (ATCC 42492) inoculum was prepared by flooding a 7-day-old culture of the fungus with 9 ml of sterile distilled water and gently removing spores with a sterile pipette tip to yield a final inoculum density of approximately $1\times10^6$ spores/ml. $R_0$ transgenic tobacco plants, grown in an environmentally controlled growth chamber, were inoculated by placing 10 drops of 10 $\mu$l each onto the adaxial surface of young, but fully developed tobacco leaves. In each experiment, leaves of at least three pBI121-transformed tobacco plants were also inoculated to serve as a negative control. Inoculated leaves were then covered with a plastic bag for 4 days. Disease severity was scored for each inoculation site of each leaf separately 7 days after inoculation using an arbitrary scale from 0 (no visible symptoms) to 5 (necrotic lesion >5 mm in diameter). One-way ANOVA was used to determine the effect of transgenic plants on disease severity. Mean separation was performed using the method of Tukey (Sokal et al., supra).

Figure 6:
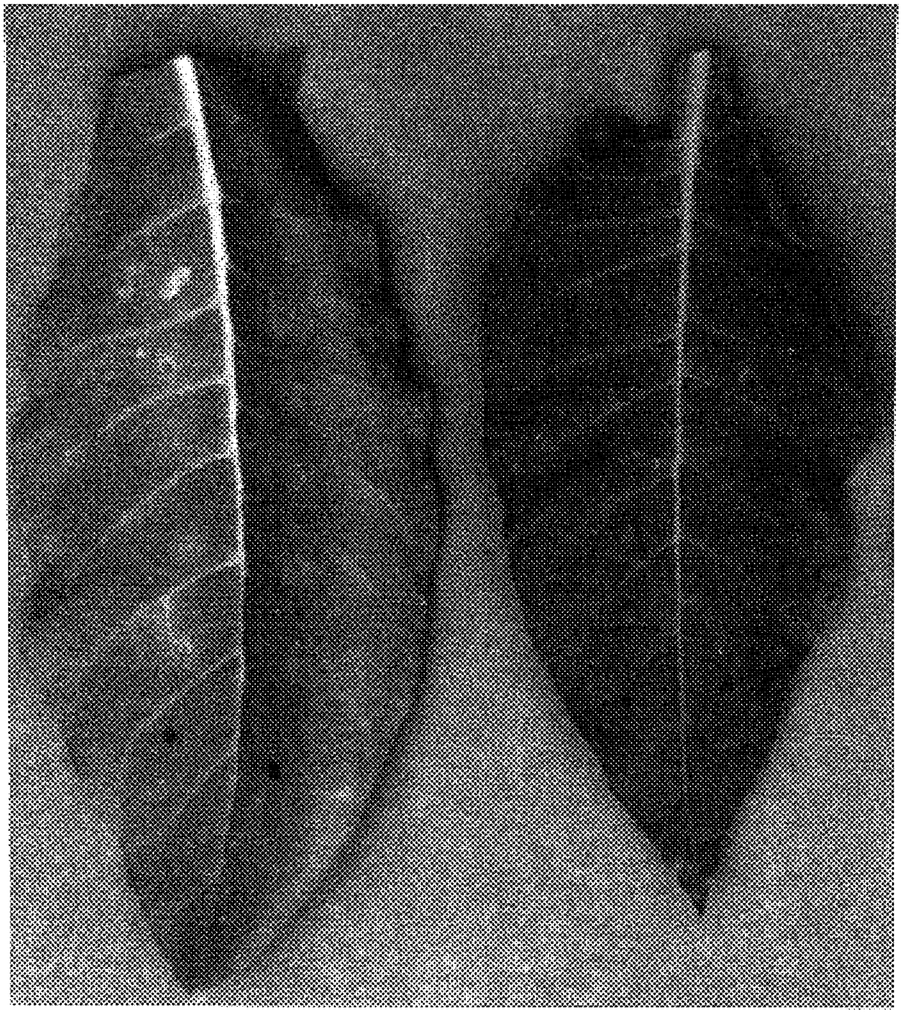
FIG. 6 shows tobacco leaves (cv. Xanthi) from a control tobacco plant transformed with pBI121 and a transgenic plant (H7), both showing anthracnose symptoms 7 days after inoculation.
Figure 7:
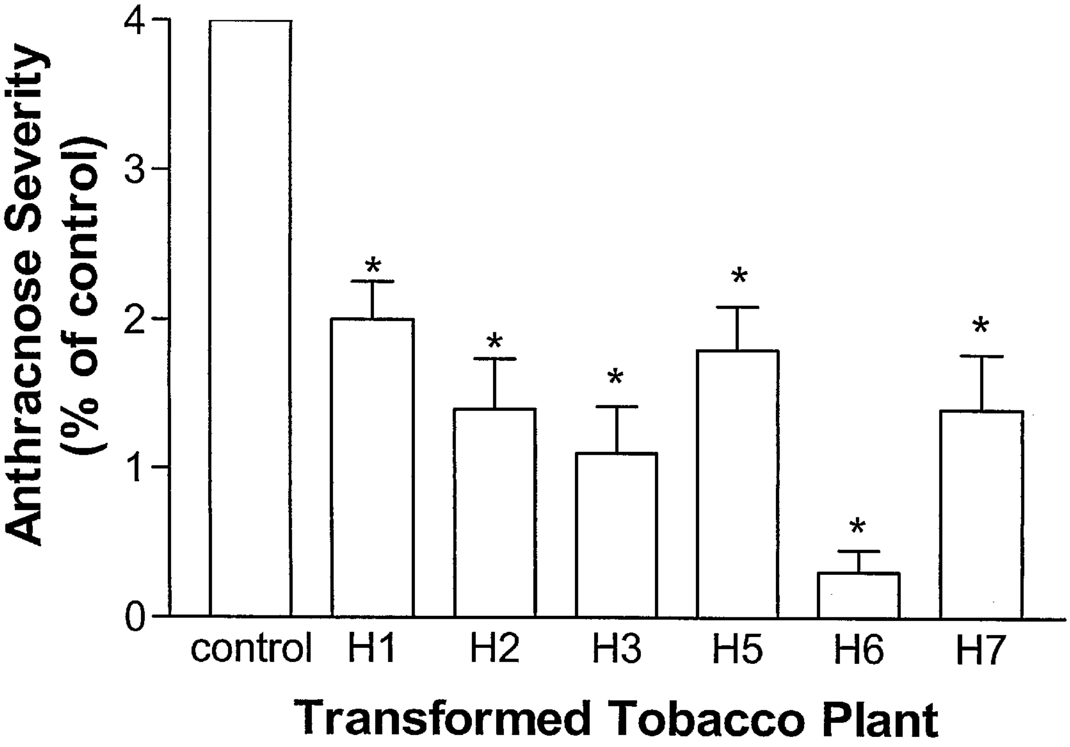
FIG. 7 shows anthracnose severity among tobacco plants transformed with cpo gene construct compared with the negative control (C). Asterisk (*) indicates significant difference (P<0.05) in anthracnose severity form the negative control plant as determined by Tukey's ANOVA. Mean values from ten inoculation sites are given.

Leaves inoculated with *C. destructivum* developed anthracnose lesions within 48–72 hr after inoculation. One-way analysis of variance indicated that all the transformants showed significantly reduced ($P<0.05$) anthracnose severity compared with the controls (FIGS. 6, 7). Lesions developed more slowly on plants transformed with cpo than on the non-transformed or pBI121-transformed controls (data not shown).

Example 9

Agrobacterium-mediated Transformation of Cotton Seedling Explants

The seedling cotyledon and hypocotyl segments of cotton (*Gossypium hirsutum* L.), used for Agrobacterium transformations, were prepared from five to seven days old seedlings. The transformation procedures followed those of Rajasekaran et al. (1996. *Mol. Breed.* 2: 307–319). The selection for transformed callus colonies was accomplished by using the antibiotic G418 (Gibco BRL, Life Technologies, Gaithersburg, Md.) at 10 mg/l.

The explants were treated with Agrobacterium suspension (see Example 1) for 15 to 30 min, blotted dry, and then plated on 12 cm dia filter paper (Whatman #1) placed on freshly made, agar-solidified callus induction medium in 15 cm dia Petri dishes containing 60 ml of medium. Cocultivation was carried out for 48 h in a Percival incubator maintained at 26±2° C., 16 h light, 60–90 $\mu$E $m^{-2}s^{-1}$. Following cocultivation, the explants were thoroughly washed, blotted dry and placed on freshly prepared callus induction medium containing the selection agent (G418) and other antibiotics to control the bacterial growth according to the procedure (Rajasekaran et al., supra). NPTII ELISAs were carried out to identify transformed callus colonies, from which somatic embryos and plantlets were obtained following the procedures of Rajasekaran et al., supra. The regenerated plants were also assayed for the presence of NPTII. Several putative transformed cotton plants were transferred to the greenhouse where they flowered and set seed similar to control plants. Molecular analyses were carried out on six $R_0$ plants, labeled C615, C621, C625, C634, C635 and C640. Immature bolls from three plants, C621, C625 and C634 were utilized in the disease resistance assays against the wilt pathogen, *Verticillium dahliae* and a mycotoxin-producing fungus *Aspergillus flavus.*

Example 10

Southern Blot Analysis of Genomic DNA of Cotton Leaf Tissue

For southern blot analysis, cotton genomic DNA (20 $\mu$g) was digested to completion with EcoRI and electrophoresed on a 1% agarose gel. DNA was transferred to nylon membranes (Schleicher & Schuell, Keene, N.H.) by vacuum transfer and hybridized with the 836 bp random-primed, $^{32}$P-labeled, cpo gene PCR product.

Figure 8:
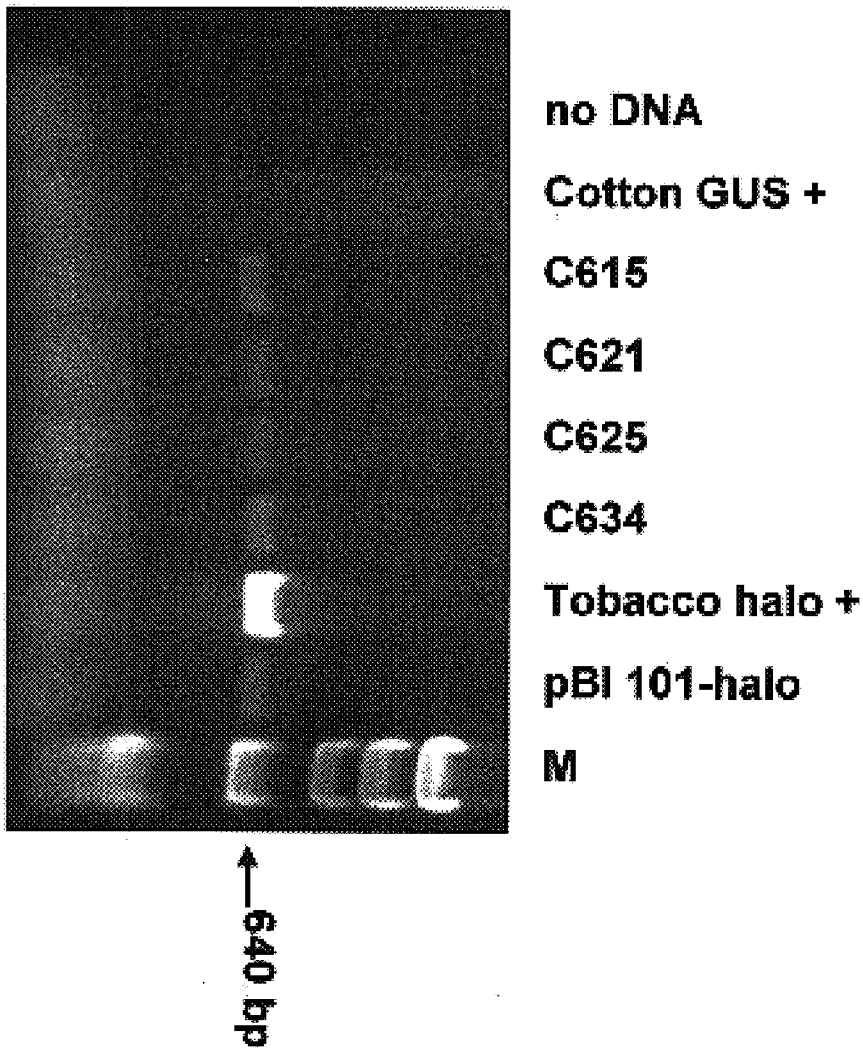
FIG. 8 shows a southern hybridization of cotton genomic DNA with a radiolabeled cpo gene probe. Genomic DNA of cotton leaf tissue transformed with pBI-d35S-halo-nos (20 μg) was digested to completion with EcoRI, electrophoresed, blotted to nylon membrane, and hybridized with the $^{32}$P-labeled 836 bp cpo gene PCR probe. Lanes: 1, no DNA(negative control); 2, transgenic cotton expressing GUS gene (negative control); 3, cotton plant C615; 4, cotton plant C621; 5, cotton plant C625; 6, cotton plant C634; 7, transgenic tobacco plant expressing halo (positive control); 8, pBI-halo plasmid DNA; and M, marker lane. HindIII-digested lambda DNA (in kbp) was used as molecular size standard.

Agarose gel electrophoresis of PCR products from the transgenic plant samples showed the expected PCR product of 640 bp representing the region of DNA spanning from within the CaMV promoter to 400 bp into the cpo gene. The no-DNA sample (Lane 1) and the negative control DNA from transgenic cotton expressing the GUS gene (Lane 2) did not show this product. Southern blot analysis of EcoRI-digested plant genomic DNA from transgenic cotton plants C615, C621, C625, and C634 and a transgenic tobacco plant showed that leaf tissue from the transgenic cotton plants gave a single hybridization signal with the radiolabeled cpo gene probe, a signal identical to that of the pBI101-halo plasmid DNA (FIG. 8). All of the transformed plants appeared to have only one copy of the cpo gene integrated into the plant genome.

Example 11

RT-PCR of Total RNA of cpo Transformed Cotton Plants

Figure 9:
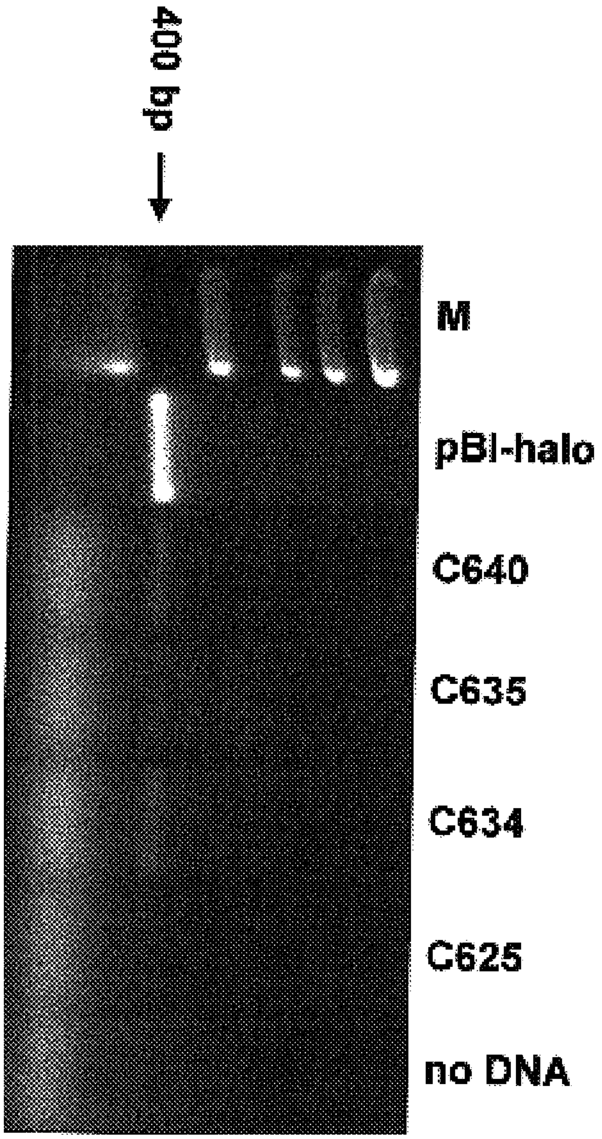
FIG. 9 shows the RT-PCR analysis of expression of the halo gene in transgenic cotton plants C640, C635, C634, and C625. The ethidium bromide stained polyacrylamide gel demonstrates the presence of an approximately 400 bp PCR product amplified from transgenic cotton cDNA following reverse transcription of total RNA. Plasmid pBI-halo-nos was used as a positive control.

Transgenic cotton plants C640, C635, C634, and C625 were analyzed for expression of the halo gene. RT-PCR analysis demonstrated the presence of an approximately 400 bp PCR-amplified product from transgenic cotton cDNA following reverse transcription of the total RNA. Plasmid pBI-halo-nos was used as the positive control (FIG. 9).

Example 12

Evaluation of CPO-P Enzyme Activity in Transgenic Cotton Leaf Extracts

Leaves of transgenic cotton plants were prepared and analyzed as described for tobacco leaves in Example 6.

CPO-P activity was observed in transgenic cotton plants, but not in the negative control plants, see Table 3 below. Occasionally a transgenic plant does not express the transgene, e.g. transgenic 612.

TABLE 3

CPO—P Activity in Control and Transgenic Cotton Leaves

| Plants | Units of enzyme/g of tissue[a] |
|---|---|
| Controls | 0 |
| 612 | 0 |
| 615 | 15.9 |
| 621 | 19.6 |
| 625 | 18.3 |
| 634 | 13.5 |
| 635 | 14.7 |

[a]One unit of enzyme is defined as the amount that catalyzes the formation of 10 nanomole monochloro-monobromodimedon/hr. Data from independent measurements differed by less than 5%.

Example 13

In Vitro Analysis of Antifungal Activity of Extracts of Transgenic Cotton Plants The inhibitory activity of extracts from cotton plants transformed with the cpo gene was assessed in vitro. Immature seeds were obtained from primary transformants representing a segregating population of R1. Fibers were removed from the seeds and were ground in liquid nitrogen. 500 $\mu$l of 1% (w/v) potato dextrose broth (PDB) at pH 6.00 was added to the ground seed. The mixture was vortexed, incubated 15 min, and centrifuged at 10,000 rpm for 10 min. An extract was collected from each sample. Control samples consisted of extract from control, non-transformed cotton plants. Pre-germinated conidial suspensions ($10^5$ conidia/ml) of *Verticillium dahliae* were then added to 225 $\mu$l of plant extract, mixed, and incubated for 60 min at RT. Three to four 50 $\mu$l aliquots from each sample tested were then plated onto PDA plates. Fungal colonies were enumerated after a 48 hr incubation at RT. Viable colonies were counted and reported as a percent of the number of colonies counted from the control, non-transformed plant extract.

Plant extracts from cotton plants transformed with the cpo gene significantly reduced ($P<0.05$) the number of fungal colonies arising from germinating conidia of *V. dahliae* compared with the extracts from the control (Table 4).

TABLE 4

| Transgenic Cotton Plants Showing Anti-*Verticillium dahliae* Activity | |
|---|---|
| Plant[a] | CFU (% of Control) |
| Control | 100 |
| C621 | 70* |
| C625 | 72* |
| C634 | 80* |

[a]Each plant tested was at least three times. Eleven seeds/plant were assayed in each experiment.
*Indicates a significant difference from Control (P < 0.05) as determined by the Wilcoxin Rank-Sum Test (Non-Parametric ANOVA).

Example 14

In Planta Cottonseed Antifungal Assay for *Aspergillus flavus*

*Aspergillus flavus* inoculum was prepared by flooding a 7-day-old culture of the fungus with 9 ml of sterile distilled water and gently removing conidia with a sterile pipette tip to yield a final inoculum density of approximately $1\times10^4$ conidia/ml. For the seed colonization assay, cottonseeds (ca. 21 dpa) were collected from control and putative transgenic cotton plants and fibers were removed. Individual cottonseeds were wounded with a sterile needle, and 5 $\mu$l of a $2\times10^4$ conidia/ml suspension of a strain of *A. flavus*, which expresses a green fluorescent protein (GFP), was pipetted into the seed. Seeds were incubated on moist filter papers at 28° C. for 7 days prior to evaluation of fungal colonization and GFP expression. The inner seed coat of each inoculated seed was examined using an Olympus SZH10 GFP-stereomicroscope. Fungal colonization was scored on a 0–4 scale (0=0%, 1=1–25%, 2=26–50%, 3=51–75% 4=76–100% of the inner seed coat surface covered with fluorescent mycelium). For fluorometric analysis, samples that were assayed for GFP expression were ground in liquid nitrogen and diluted 1:2 with phosphate buffer (50 mM, pH=7.00). Samples were mixed and centrifuged at 10,000 g for 10 min. The supernatant was collected and fluorescence determined using a Perkin-Elmer HTS 7000 fluorometer providing excitation at 485 nm and emission at 535 nm.

Seeds inoculated with *A. flavus* developed colonies within 7 days after inoculation. One-way analysis of variance indicated that the transformants C621 and C625 showed significantly reduced (P<0.05) severity of infection compared with the controls, Table 5.

TABLE 5

| Colonization of *A. flavus*70-GFP in Cotton Seeds from Plants Transformed with Haloperoxidase. | | |
|---|---|---|
| Plant[a] | Incidence of Severly Infected Seeds | Seedcoat Fluorescence |
| Control | 0.49 ± 0.09 | 100.0 ± 0.2 |
| C621 | 0.09 ± 0.09* | 34.5 ± 7.1* |
| C625 | 0.17 ± 0.14* | 58.8 ± 20.6* |
| C634 | 0.21 ± 0.15* | 79.6 ± 18.3 |

[a]Each plant was tested at least three times. Eleven seeds/plant were assayed in each experiment.
*Indicates a significant difference from the control (P < 0.05) as determined by the Wilcoxin Rank-Sum test (Non-Parametric ANOVA).

It is understood that the foregoing detailed description is given merely by way of illustration and that modifications and variations may be made therein without departing from the spirit and scope of the invention.

We claim:

1. A pathogen-resistant transgenic plant expressing nonheme chloroperoxidase from *Pseudomonas pyrrocinia*, wherein the nonheme chloroperoxidase is expressed at a level sufficient to induce pathogen resistance.

2. A pathogen-resistant transgenic plant comprising plant cells containing a DNA segment encoding a nonheme chloroperoxidase of Pseudomonas, wherein the DNA segment has 95% sequence identity to SEQ ID NO:1, and wherein the nonheme chloroperoxidase is expressed at a level sufficient to induce pathogen resistance.

3. The pathogen-resistant transgenic plant according to claim 2, wherein the nonheme chloroperoxidase is SEQ ID NO:2.

4. The pathogen-resistant transgenic plant according to claim 2, wherein the DNA segment encoding a nonheme chloroperoxidase is SEQ ID NO:1.

5. A plant part from the transgenic plant according to claim 2, wherein the plant part contains the DNA segment encoding a nonheme chloroperoxidase.

6. The plant part of claim 5 selected from the group consisting of leaves, stems, roots, flowers, tissues, epicotyls, meristems, hypocotyls, cotyledons, pollen, ovaries, cells, and protoplasts.

7. A plant part which can be regenerated to form a fertile plant, wherein the plant part expresses the DNA segment according to claim 2.

8. A progeny plant produced by sexual or asexual reproduction of the plant of claim 2, wherein the progeny plant comprises the DNA segment encoding a nonheme chloroperoxidase.

9. A transgenic seed of the transgenic plant according to claim 2.

10. A pathogen-resistant transgenic plant comprising plant cells containing a chimeric construct comprising a promoter operable in said plant cells, said promoter is operably linked to a DNA segment encoding a nonheme chloroperoxidase of *Pseudomonas pyrrocinia*, wherein the DNA segment is expressed at a level sufficient to induce pathogen resistance.

11. The pathogen-resistant transgenic plant according to claim 10, wherein the nonheme chloroperoxidase is SEQ ID NO:2.

12. The pathogen-resistant transgenic plant according to claim 10, wherein the DNA segment encoding a nonheme chloroperoxidase Is SEQ ID NO:1.

13. The pathogen-resistant transgenic plant according to claim 10, wherein the chimeric construct further comprises a 5' untranslated region containing a translational enhancer, and a 3' untranslated region containing a functional polyadenylation signal.

14. The pathogen-resistant transgenic plant according to claim 10, wherein the chimeric construct further comprises DNA encoding a selective marker.

15. The pathogen-resistant transgenic plant of claim 10, further comprising a heterologous coding sequence of interest.

16. A plant part from the transgenic plant according to claim 10, wherein the plant part contains the chimeric construct.

17. The plant part of claim 16 selected from the group consisting of leaves, stems, roots, flowers, tissues, epicotyls, meristems, hypocotyls, cotyledons, pollen, ovaries, cells, and protoplasts.

18. The plant part according to claim 17, wherein the plant part can be regenerated to form a fertile plant, wherein the fertile plant contains the chimeric construct.

19. A progeny plant produced by sexual or asexual reproduction of the plant of claim 10, wherein the progeny plant comprises the chimeric construct.

20. A transgenic seed of the transgenic plant according to any one of claims 10–15.

21. The plant according to claim 10, wherein the promoter is selected from the group consisting of a promoter which is constitutive and a promoter which is inducible.

22. The plant according to claim 10, wherein the promoter is selectively active in a tissue selected from the group consisting of leaf, root, and seed.

23. A method of making a pathogen-resistant plant, said method comprising:

providing a plant cell capable of regeneration;

transforming said plant cell with a DNA segment encoding a nonheme chioroperoxidase of *Pseudomonas pyrrocinia;* culturing said plant cell under plant cell growing conditions;

regenerating from said plant cell a plant; and observing expression of said DNA segment in said plant, whereby the DNA segment is expressed at a level sufficient to make a pathogen-resistant plant.

24. The method according to claim 23, wherein the DNA segment encoding a nonheme chloroperoxidase has at least 95% sequence identity to SEQ ID NO:1.

25. The method according to claim 23, wherein the DNA segment encoding a nonheme chloroperoxidase is SEQ ID NO:1.

26. The method according to claim 23, wherein said transforming step is carried out by bombarding said plant cell with microparticles carrying said DNA segment.

27. A method of making a pathogen-resistant plant, said method comprising:

providing a plant cell capable of regeneration;

transforming said plant cell with a chimeric construct comprising a promoter operable in said plant cell, said promoter is operably linked to a DNA segment encoding a nonheme chloroperoxidase of *Pseudomonas pyrrocinia;* culturing said plant cell under plant cell growing conditions;

regenerating from said plant cell a plant; and observing expression of said DNA segment in said plant, whereby the DNA segment is expressed at a level sufficient to make a pathogen-resistant plant.

28. The method according to claim 27, wherein the DNA segment encoding a nonheme chloroperoxidase has at least 95% sequence identity to SEQ ID NO:1.

29. The method according to claim 27, wherein the DNA segment encoding a nonheme chloroperoxidase is SEQ ID NO:1.

30. The method according to claim 27, wherein said transforming step is carried out by bombarding said plant cell with microparticles carrying said chimeric construct.

31. The method according to claim 27, wherein said transforming step is carried out by infecting said cell with an *Agrobacterium tumefaciens* containing a Ti plasmid carrying said chimeric construct.

32. The method according to claim 27, wherein the promoter is selected from the group consisting of a promoter which is constitutive and a promoter which is inducible.

33. A pathogen-resistant transgenic cotton plant comprising cotton plant cells containing a chimeric construct comprising a promoter operable in said plant cells, said promoter is operably linked to a DNA segment encoding a nonheme chloroperoxidase of *Pseudomones pyrrocinia*, wherein the DNA segment is expressed at a level sufficient to induce pathogen resistance.

34. The method according to claim 33, wherein the DNA segment encoding a nonheme chloroperoxidase has at least 95% sequence identity to SEQ ID NO:1.

35. The method according to claim 33, wherein the DNA segment encoding a nonheme chloroperoxidase is SEQ ID NO:1.

* * * * *